US006372502B1

United States Patent
Bank et al.

(10) Patent No.: US 6,372,502 B1
(45) Date of Patent: *Apr. 16, 2002

(54) RETROVIRAL PACKAGING CELL LINES AND PROCESSES OF USING SAME

(75) Inventors: Arthur Bank, Riverdale; Dina G. Markowitz, New York, both of NY (US); Stephen P. Goff, Tenafly, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/341,269

(22) Filed: Nov. 17, 1994

Related U.S. Application Data

(63) Continuation of application No. 08/048,926, filed on Apr. 16, 1993, now abandoned, which is a continuation of application No. 07/887,410, filed on May 20, 1992, now abandoned, which is a continuation of application No. 07/623,275, filed on Dec. 6, 1990, now abandoned, which is a continuation of application No. 07/207,119, filed on Jun. 15, 1988, now abandoned, which is a continuation-in-part of application No. 07/152,830, filed on Feb. 5, 1988, now abandoned.

(51) Int. Cl.$^7$ ............................................... C12N 15/87
(52) U.S. Cl. ....................... 435/465; 435/455; 435/325; 435/354; 435/357
(58) Field of Search ........................... 435/172.3, 240.1, 435/240.2, 325, 455, 465, 354, 357

(56) References Cited

U.S. PATENT DOCUMENTS

| | | | | |
|---|---|---|---|---|
| 4,650,764 A | * | 3/1987 | Temin et al. ................ | 435/240 |
| 4,861,719 A | * | 8/1989 | Miller ................. | 435/320.1 X |
| 5,278,056 A | * | 1/1994 | Bank et al. .............. | 435/172.3 |

OTHER PUBLICATIONS

Hesdorffer et al., Journal of Clinical Oncology 16(1):165–172 (1998).*
Chong et al., Gene Therapy 3: 624–629 (1996).*
Watanabe et al (1983) Mol Cell Biol 3:2241–2249.*
CA 87:17475C (1977) Efstratiatis et al.*
Mann et al (1983) Cell 33:153–159.*
Miller et al (1986) Som Cell Mol Genet 12:175–183.*
Pouwels et al Eds (1985) in Cloning Vectors (8 pages).*
R.A. Hock, et al. (1986) Nature, 320:275.
R.C. Mulligan and P. Berg, (1980) Science, 209:1422.
G. Keller et al., (1985) Nature, 318:145.
H.E. Gruber et al., (1985) Science, 230:237.
D.A. Williams et al. (1984) Nature, 310:476.
D.A. Williams et al. (1986) Science, 83:2566.
M.A. Eglitis et al. (1985) Science, 230:1395.
Miller et al. Som. Cell and Mol. Gen. vol. 12, No. 2: pp. 175–183, 1986.*
Mann et al. Cell vol. 33: pp. 153–159, 1983.*
Pouwels. Cloning Vectors: A Laboratory Manual. pp. VIII–1–VIII–7. Elsevier, Amsterdam, 1985.*

* cited by examiner

*Primary Examiner*—Remy Yucel
(74) *Attorney, Agent, or Firm*—John P. White; Cooper & Dunham LLP

(57) ABSTRACT

This invention provides a mammalian cell useful for retroviral packaging comprising two plasmids, both of which comprise the 5' long terminal repeat (LTR) sequence from a helper virus, neither of which comprise a functional ψ packaging sequence or a 3' LTR from the helper virus, one of which comprises the env gene from the helper virus and the other of which comprises the gag and pol genes from the helper virus. This invention also provides a process for preparing a producer cell useful for transferring a foreign gene into a mammalian cell which comprises treating the above-described mammalian cell with a vector plasmid so as to insert the vector plasmid into the cell and thus create the producer cell, the vector plasmid comprising the foreign gene, a functional ψ packaging sequence from the helper virus, both the 5' and 3' LTRS from the helper virus, and a gene encoding a selectable or identifiable phenotypic trait, and recovering the producer cell so created.

6 Claims, 5 Drawing Sheets

RETROVIRAL PACKAGING CELL LINES AND PROCESSES OF USING SAME

This application is a continuation of U.S. Ser. No. 08/048,926, filed Apr. 16, 1993, now abandoned which is a continuation of U.S. Ser. No. 07/887,410, filed May 20, 1992, now abandoned, which is a continuation of U.S. Ser. No. 07/623,275, filed Dec. 6, 1990, now abandoned, which is a continuation of U.S. Ser. No. 07/207,119, filed Jun. 15, 1988, now abandoned, which is a continuation-in-part of U.S. Ser. No. 07/152,830, filed Feb. 5, 1988, now abandoned.

The invention described herein was made in the course of work under Public Health Services grants DK-25274, HL-37069, and HL-07230 from the National Institutes of Health, U.S. Department of Health and Human Services. The U.S. Government has certain rights in this invention.

BACKGROUND OF THE INVENTION

Throughout this application, various publications are referenced parentheses and citations provided for them. The disclosure of these publications in their entireties are hereby incorporated by reference into this application to more fully describe the state of the art to which this invention pertains.

Retroviruses appear to be the method of choice as vectors for the transfer of exogenous genes into humans. In particular, the cloning, transfer, and expression of human globin genes into erythroid cells in culture has raised the possibility of autotransplantation of bone marrow cells with normal β-globin genes as an approach to the therapy of β-thalassemia and sickle cell anemia in humans (1). Retroviral vectors are the most efficient means of transferring genes into cells. This high efficiency is a requirement for experiments whose goal is human globin gene therapy because only a limited number of bone marrow stem cells can be obtained, and as many as possible must acquire and express the transferred genes to ensure repopulation of sufficient marrow elements to produce normal amounts of hemoglobin.

A major prerequisite for the use of retroviruses is to insure the safety of their use (2). The major danger of the use of retroviruses for gene therapy is the possibility of the spread of wild-type retrovirus in the cell population. The proliferation of wild-type virus can lead to multiple integrations of the retrovirus into the genome which may result in the activation of potentially harmful genes such as oncogenes (3,4). The development of packaging cell lines that produce only replication-defective retroviruses has increased the utility of retroviruses for gene therapy (5–9). In these cell lines, the sequence required for packaging of the viral RNA (ψ sequence) has been deleted, therefore, the packaging cell produces viral proteins but is unable to package the viral RNA genome into infectious virions. When these packaging lines are transfected with a replication-defective retroviral vector containing an intact ψ sequence required for its own packaging, wild-type retrovirus has been shown to arise (6,10,11) presumably due to recombination events between the helper virus genome and the vector virus. For example, high titer amphotropic retroviral stocks generated by transfer of a defective neomycin-containing retrovirus into the amphotropic packaging cell line PA12 (containing the ψ deletion) have been shown to produce infectious amphotropic helper virus (10,11). To circumvent this problem, additional mutations have been made in the defective virus of newer helper cell lines (11). These have included deletions in the 3' LTR of the helper virus component, and additional deletions of portions of the 5' LTR as well. One of these defective amphotropic constructs has been used to produce a retroviral packaging line, PA317, that has recently been reported to eliminate wild type retrovirus production after retroviral transfection. However, using this packaging line, two recombinational events could still produce intact retrovirus. Cell lines containing both 3' and 5' LTR deletions as well as the packaging mutation were also constructed but were not useful because of the relatively low titers obtained with these constructs.

In accordance with the invention described herein, novel ecotropic and amphotropic retrovirus packaging cell lines have been created which should virtually eliminate the possibility of recombination between the helper virus and the vector virus leading to wild-type retrovirus. In the cell lines to be described hereinafter, the helper virus DNA has been separated onto two plasmids; the gag and the pol genes are on one plasmid and the env gene is on another plasmid. In addition, the packaging sequence and the 3' LTR have been deleted in both plasmids. With this type of strategy at least three recombination events between the two helper plasmids and the vector virus are necessary to generate a wild-type virus. Thus, stable ecotropic and stable amphotropic packaging lines have been developed that are both efficient and safe for use in gene transfer experiments. An ecotropic packaging line has been developed. In such a line the virus can only infect or transfect cells of the same species. In an amphotropic packaging line, the virus can infect or transfect a wide range of host cell species.

SUMMARY OF THE INVENTION

The invention concerns a mammalian cell useful for retroviral packaging comprising two plasmids, both of which comprise the 5' long terminal repeat (LTR) sequence from a helper virus, neither comprise a functional ψ packaging sequence or a 3' LTR from the helper virus, one of which comprises the env gene from the helper and the other of which comprises the gag and pol genes from the helper virus.

The invention also provides a process for preparing a producer cell useful for transferring a foreign gene into a mammalian cell which comprises treating the above described mammalian cell with a vector plasmid so as to insert the vector plasmid into the cell and thus create the producer cell, the vector plasmid comprising the foreign gene, a functional ψ packaging sequence from the helper virus, both the 5' and 3' LTRs from the helper virus, and a gene encoding a selectable or identifiable phenotypic trait, and recovering the producer cell so created.

DETAILED DESCRIPTION OF THE INVENTION

This invention concerns a mammalian cell useful for retroviral packaging comprising two plasmids, both of which comprise the 5' long terminal repeat (LTR) sequence from a helper virus, neither of which comprise a functional $\psi$ packaging sequence or a 3' LTR from the helper virus, one of which comprises the env gene from the helper virus and the other of which comprises the gag and pol genes from the helper virus.

In one embodiment of this invention one of the plasmids in the above-described mammalian cell further comprises a gene encoding a selectable or identifiable phenotypic trait. An example useful in the practice of the present invention is the gpt gene. In another embodiment, the helper virus in the mammalian cell is the Moloney murine leukemia virus (Mo-MuLV).

Figure 2:
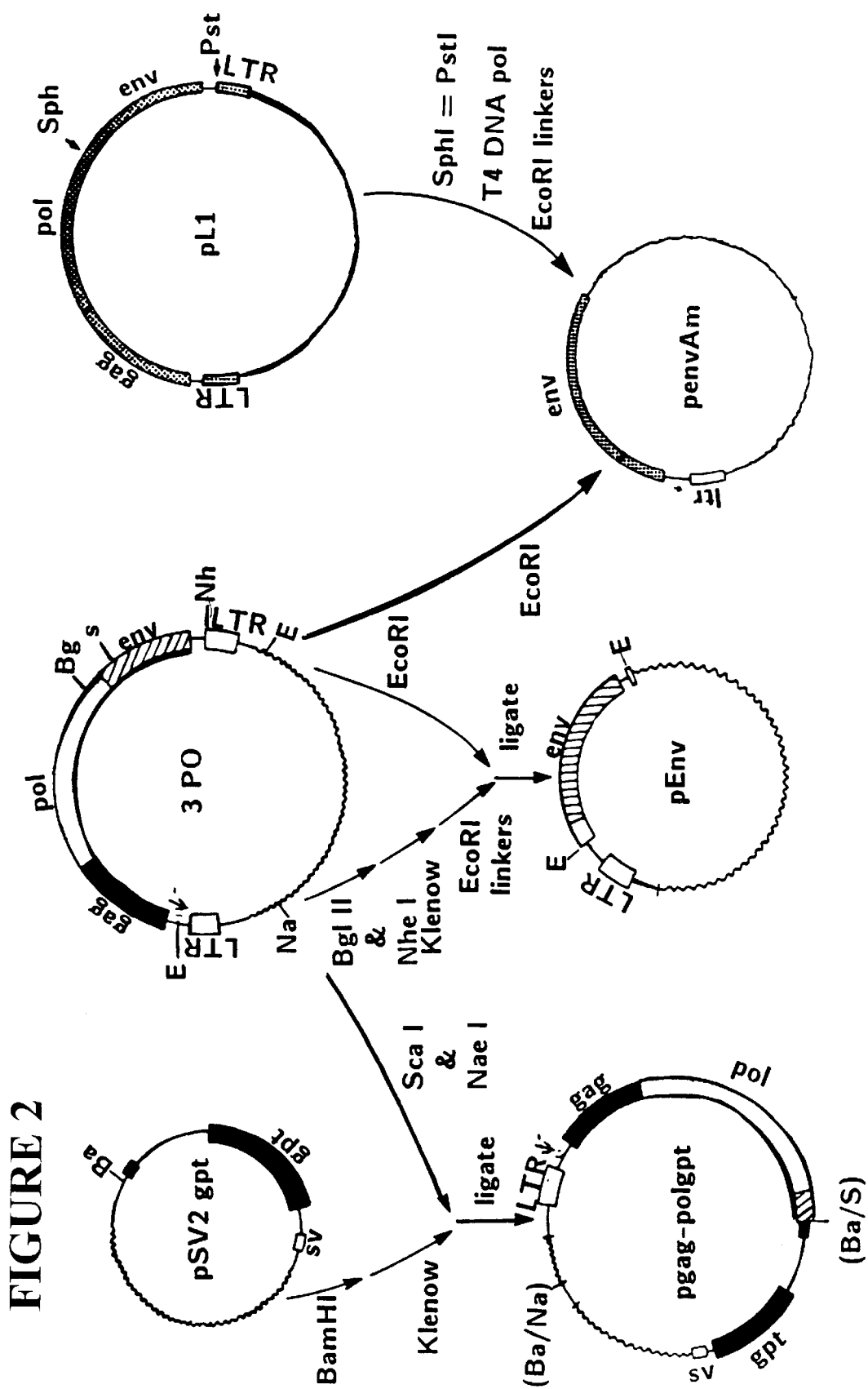
FIG. 2. Schematic diagram showing construction of plasmids pgag-polgpt, penv, and penvAm. Wavy lines, pBR322 sequences; thin lines, plasmid sequences; small solid box, SV40 poly A sequences; SV, SV40 origin of replication; ψ-, deletion of ψ packaging sequences; Ba, Bam HI; Bg, Bgl II; E, Eco RI: Na, Nae I; Nh, Nhe I; S, Sca I; Sph, Sph I; Pst, Pst I.

In other aspects, the one plasmid in the mammalian cell is the plasmid designated penv shown in FIG. 2, and the other plasmid is the plasmid designated pgag-polgpt also shown in FIG. 2.

The mammalian cell of this invention may be an ecotropic cell, including an NIH 3T3 mouse fibroblast cell. Where the helper virus in the mammalian cell is the Moloney murine leukemia virus (Mo-MuLV), such an ecotropic cell useful in the practice of this invention is designated GP+E-86. The ecotropic cell, GP+E-86, has been deposited Feb. 4, 1988 pursuant to the Budapest Treaty at the American Type Culture Collection (ATCC), Rockville, Md., in NIH 3T3 Mouse Fibroblast Cells under ATCC accession no. CRL 9642.

In another feature, the helper virus in the mammalian cell is the 4070A amphotropic murine leukemia virus. In further embodiments where the 4070A amphotropic murine leukemia virus is employed as the helper virus, the one plasmid is the plasmid designated penvAm shown in FIG. 2, and the other plasmid is the plasmid designated pgag-polgpt, also shown in FIG. 2.

In another embodiment, the invention herein further provides an amphotropic cell as the mammalian cell useful for retroviral packaging. An example of an amphotropic cell useful in the practice of this invention is designated GP+envAm-12. The amphotropic cell, GP+envAm-12, has been deposited Feb. 14, 1988 pursuant to the Budapest Treaty at the American Type Culture Collection (ATCC), Rockville, Md., in NIH Mouse Fibroblast Cells under ATCC accession no. CRL 9641.

The mammalian cells of this invention may be constructed from "parent" plasmids, e.g., pSV2Gpt, 3PO and pL1 using methods well known to those skilled in the art. For example, the plasmid, pgag-polgpt, may be constructed using the plasmid pSV2gpt (12) as the source of SV40 sequences and the gpt gene as the selectable marker, and the 3PO plasmid. The latter plasmid, 3PO, contains Mo-MuLV proviral DNA with a 134 base pair deletion of the $\psi$ packaging signal, from the restriction sites, Bal I 660 to Xma III 794 (L. Lobel and S. Goff). The parent plasmids can be "cut" with restriction enzymes. Depending on the starting plasmid and the particular restriction enzyme employed, the resulting fragments may be blunt-ended. Alternatively, if not blunt-ended, the protruding end of the plasmid may be filled in, again employing techniques well-known in the art, such as using the Klenow fragment of DNA polymerase and all four deoxynucleoside triphosphates (dNTPs). The resulting fragments may then be ligated together and positive colonies isolated using, for example, colony filter hybridization (18) and then probing using complementary fragments. In isolating colonies using filter hybridization, the probe is labelled, e.g., radioactively labelled or using other conventional labelling well known to those skilled in the art.

The penv plasmid may also be constructed using the 3PO parent plasmid alone. In this instance, the 3PO plasmid is digested with restriction enzymes, e.g., Bgl II and Nhe I and the resulting fragment of approximately 2.4 kilobases is isolated from the gel by electroelution. The ends are then filled in using, four example, Klenow polymerase and all four dNTPs.

After their preparation, as described above, the plasmids are introduced into cultured mammalian cells, e.g., mouse fibroblast cells, in particular NIH 3T3 cells. The methods of introduction are well known in the art and include, as an example, transfection, specifically electroporation. Typically, the cultured mammalian cells are collected by centrifugation and resuspended in a buffer solution, e.g., PBS. The cells are then mixed with the nonselectable plasmid DNA and/or the selectable plasmid DNA. The suspension of cells and DNA so formed is loaded into an electroporation apparatus, such as 0.5 ml PDS model ZA1000, Prototype Design Services, P.O Box 55355, Madison, Wis., 53705, and a bank of capacitors, charged to several hundred volts, e.g., 500–1000 volts, and discharged via an electronic switch through the solution. After electroporation, the transformed cells are resuspended in supplemented medium, suitable quantities of appropriate antibiotics and plated, for example, in well plates. Selective media is added approximately 48–72 hours after electroporation.

The two plasmids, pgag-polgpt and penv may be stably introduced by coelectroporation, i.e., at the same time, into cultured mammalian cells, e.g., mouse fibroblast cells, NIH 3T3. The transformed cells are then selected for the presence of a marker gene, such as, for example, the gpt gene using HXM media, which comprises hypoxanthine, xanthine and mycophenolic acid (MA). The clones which are selected with the HXM media may then be analyzed for reverse transcriptase (RT) production, as described (14) by Goff et al., 1981, *J. Virology*, 38:239–248.

The present invention also provides a process for preparing a producer cell useful for transferring a foreign gene into a mammalian cell which comprises treating a mammalian cell, above-described, with a vector plasmid so as to insert the vector plasmid into the cell and thus create the producer cell, the vector plasmid comprising the foreign gene, a functional $\psi$ packaging sequence from the helper virus, both the 5' and 3' LTRs from the helper virus, and a gene encoding a selectable or identifiable phenotypic trait, and recovering the producer cell so created.

In one embodiment of this invention, treating the mammalian cell with a vector plasmid comprises the method of transfection. In further embodiments, the vector plasmid, that is used in the above-described process for preparing a producer cell useful for transferring a foreign gene into a mammalian cell, is a replication retroviral vector. Such replication defective retroviral vectors include the vectors designated Δneo or N2, both shown in FIG. 3. In another feature, the phenotypic trait which is encoded by a gene in the vector plasmid is drug resistance. An example of a foreign gene for use in the above-described process is the normal human β globin gene. The present invention also provides a producer cell produced by the described above process for preparing a producer cell.

Transfection may be carried out for purposes of illustration by electroporation, which has been described earlier. Mammalian cells, e.g., NIH 3T3 cells are transfected by electroporation with the vector plasmids, e.g., Δneo and N2. These plasmids contain gene encoding a selectable or identifiable phenotypic trait, such as drug or antibiotic resistance, e.g., neomycin resistance. Using the drug or antibiotic, eukaryotic cells expressing the gene are selected.

This invention also provides a method for transferring a foreign gene into a mammalian cell which comprises contacting the mammalian cell with the producer cell, described above, under conditions such that (a) the producer cell releases the foreign gene packaged in the vector plasmid, and (b) the foreign gene is introduced into the mammalian cell.

This invention also concerns a method of gene therapy comprising transferring a foreign gene encoding a therapeutic protein into a subject afflicted with a genetic disorder using the above-described method for transferring a foreign gene into a mammalian cell.

In other aspects the foreign gene in the above-described method of gene therapy encodes the normal human β globin gene and the genetic disorder is sickle cell anemia or β-thalassemia, and the vector plasmid is a retroviral vector.

The invention is illustrated in the Experimental Detail and Experimental Discussion sections which follow. These sections are set forth to aid in an understanding of the invention but are not intended to, and shall not be construed to, limit in any way the invention as set forth in the claims which follow thereafter.

EXPERIMENTAL DETAILS

Materials and Methods
Generation of Ecotropic Packaging Line
To generate an ecotropic packaging cell line two helper virus plasmids, pgag-polgpt and penv, were constructed using Mo-MULV proviral DNA from the plasmid 3PO as starting material (FIG. 1).
pgag-polgpt
pgag-polgpt (FIG. 2) was constructed by isolating a fragment containing the 5' LTR and the gag and pol DNA and inserting this fragment into the plasmid psV2gpt (12) which was used as the source of SV40 sequences and the gpt gene as a selectable marker.

The plasmid 3PO contains MO-MULV proviral DNA with a 134 base pair deletion of the ψ. packaging signal, from Bal I 660 to Xma III 794 (L. Lobel and S. Goff, personal communication). 3PO DNA was digested with Sca I and Nae I, both leaving blunt ends, and a 7.9 kilobase (kb) fragment containing the 5' LTR and the gag and pol genes were isolated from a 1.7% agarose gel by electroelution. Plasmid pSV2gpt was digested at its unique Bam HI site, and its protruding 5' ends filled by using the Klenow fragment of DNA polymerase and all four dNTPs. The 7.9 kb gag-pol fragment was then ligated to the blunt-ended 5.1 kb pSV2gpt vector, and positive colonies were isolated using colony filter hybridization (18), probing with a nick-translated 2.54 kb Bgl II fragment fro 3PO (gag-pol probe). DNAs from individual colonies were then tested for the correct orientation of the gag-pol insert by digesting with Eco RI. The resulting 13.4 kb plasmid was named pgag-polgpt (FIG. 2)
penv
penv (FIG. 1) was constructed by isolating a fragment from 3PO that contains the 3' acceptor splice site and the env gene and the ligating it to another fragment from 3PO containing the 5' LTR and 5' donor splice site.

First, the plasmid 3PO was digested with Bgl II and Nhe I (FIG. 2). The 2.4 kb env fragment 5858 to 8297 containing the 3' acceptor splice site was isolated by electroelution from a 1.2% agarose gel. The ends were filled with the Klenow fragment of DNA polymerase and all four dNTPs, and Eco RI linkers were ligated to both ends. The 5' LTR and 5' donor splice site were prepared by digesting 3PO DNA with Eco RI, and isolating the 6.2 kb fragment by electroelution from a 1% agarose gel. The 6.2 kb fragment was phosphatased, and then ligated to the 2.4 kb env fragment. Positive transformants were isolated using the colony filter hybridization technique probed with a labelled 1.2 kb Hpa I fragment from 3PO (env probe). DNAs from positive colonies were then tested for the correct orientation of the env insert by digesting with either Xba I or Sca I. The resulting 8.6 kb plasmid was named penv (FIG. 2).
Electroporation and Cell Analysis
NIH 3T3 Cells were transfected with pgag-polgpt or the penv plasmid by electroporation (13). For each experiment, $10^7$ cells were collected by centrifugation, and resuspended in 0.5 ml sterile 1×PBS. The cells were then mixed with $10^7$ μg nonselectable plasmid DNA and/or 5 μg selectable plasmid DNA. The cell/DNA suspension was loaded into a 0.5 ml electroporation chamber (PDS model ZA1000, Madison, Wis.) and a bank of capaciters (effective capacity 14UF), charged to 500–1,000 volts, and discharged via an electronic switch through the solution. The cells were then resuspended in 100 ml Dulbecco modified Eagle medium (DMEM), supplemented with 10% newborn calf serum, penicillin (100 μg/ml), streptomycin (100 μg/ml), and amphotericin B (0.25 μg/ml); and plated in four 24 well plates. Selective media was added 48–78 hours after the electroporation.

The plasmids pgag-polgpt and penv were coelectroporated into 3T3 cells; as a control, 3PO and pSV2gpt were also coelectroporated into 3T3 cells. Cells were selected for the presence of the gpt gene with media containing 15 μg/ml of hypoxanthine, 250 μg/ml of xanthine and 25 μg/ml of mycophenolic acid (MA) (HXM media). Clones selected with HXM media were then analyzed for reverse transcriptase (RT) production as described previously (14). Positive controls for RT activity were ψ2 cell (6) supernatants and supernatants from wild type Mo-MULV clone 4 cells. Negative controls for RT activity were untransfected 3T3 supernatants and RT cocktail alone.

Figure 3:
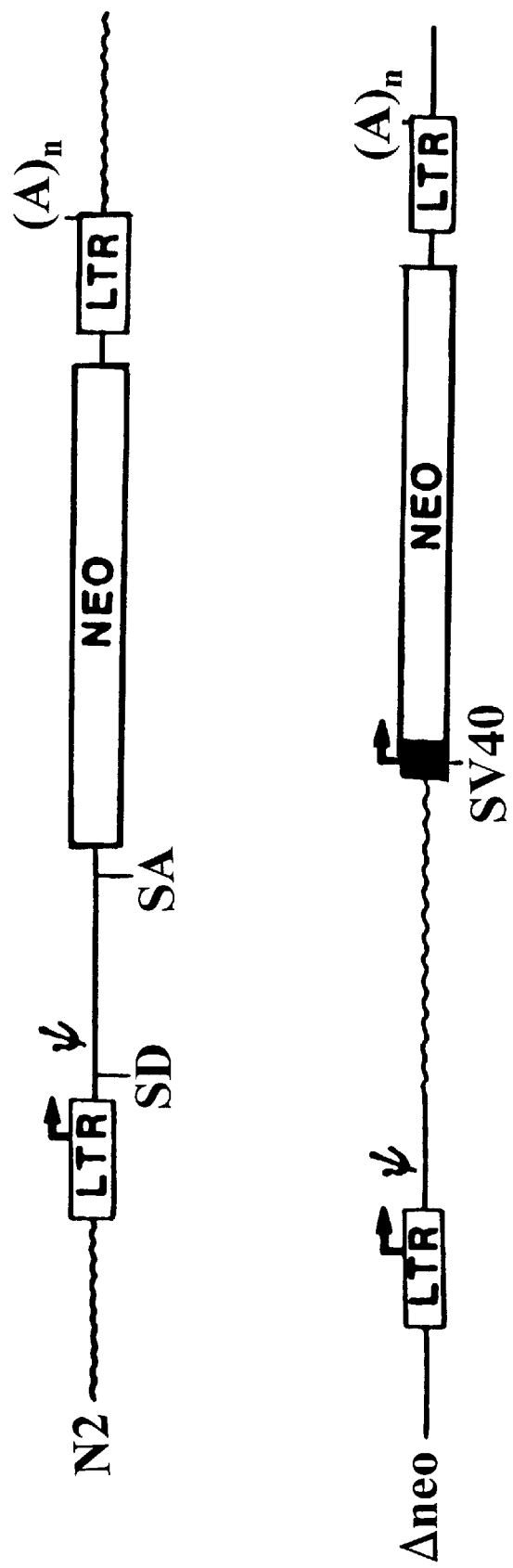
FIG. 3. Replication-defective retroviral vectors N2 and Δneo. ψ, packaging sequence; wavy line, pBR322 sequences; solid box, SV40 promoter and origin of replication.

Packaging lines were transfected with the retroviral vector plasmids Δneo and N2 by electroporation of $10^7$ NIH 3T3 cells with 5 μg plasmid DNA. Both plasmids contain a neomycin resistance ($neo^R$) gene; eukaryotic cells expressing the gene were selected with the antibiotic G418 (800 μg/ml). Δneo is a 6.6 kb replication-defective retroviral plasmid in which the neo$^R$ gene is flanked by intact LTRs and has 5' gag sequences including an intact ψ sequence (FIG. 3). (N. Lerner, personal communication); N2 has been described previously (16).

Analysis of Viral Proteins

The presence and expression of penv was analyzed by metabolic labelling and immunoprecipitation of gPr80env, the env protein, with env antiserum as follows: Clones of confluent cells (on 10 cm plates) were starved for 20 minutes in DMEM minus methionine, and 150 μc $^{35}$S methionine (Amersham) was added for 40 minutes. The cells were lysed in 1% Triton X100, 0.5% deoxycholate, 0.1% SDS, 10 mM sodium phosphate, pH 7.5, 0.1 M NaCl; the cell lysate was spun down in a TI50 or TI80 rotor at 35 K for three hours at 4° C. The supernatant was incubated with normal goat serum, and nonspecifically bound proteins precipitated with pansorbin (staph A protein, Cal-Biochem). The remaining supernatant was incubated with env antiserum (NCI #795-771) overnight and the immunoprecipitates collected with pansorbin. The labelled proteins were analyzed by electrophoresis on a 10% SDS polyacrylamide gel (19) followed by fluorography.

Virus Production

Titers of colony-forming units were determined by infection of NIH 3T3 cells dilutions of viral harvest as follows: NIH 3T3 cells (5×10$^5$) were seeded in a 6 cm petri dish. Eighteen hours later viral harvest supernatants from clones of semi-confluent cells were filtered through 0.45 micron filters (Millipore) and 1 ml was applied to the cells. Eight μg/ml of polybrene (Dextran) was added to the supernatants to enhance the titer. After 2 hours at 37° C., 4 ml of media were added to the cells; 48 hours later the cells were trypsinized and plated on a 10 cm plate in media containing 800 μg/ml G418; 10–14 days later clones were counted.

Generation of the Packaging Line

Figure 4:
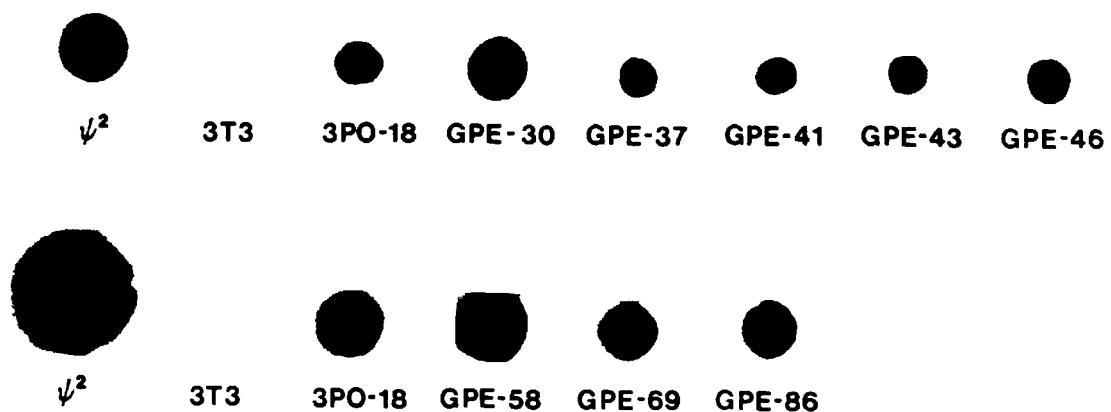
FIG. 4. RT assays of supernatants from clones of cells with 3PO or cotransfected with pgag-polgpt and penv. Individual clones resistant to MA were isolated, and the supernatant fluids were assayed for reverse transcriptase on an exogenous template (14). Results are shown from two different experiments (top and bottom lines). Included in each experiment are positive ($\psi^2$ supernatant) and negative (3T3 supernatant) controls.

To generate cell lines expressing gag-pol and env regions from different plasmids, 3T3 cells were cotransfected, by electroporation (13), with pgag-polgpt and penv DNAs. Recipient cells were then selected for the presence of the gpt gene with media containing mycophenolic acid (MA). Eighty-six MA-resistant (GP+E) clones were isolated and their supernatants tested for their ability to produce reverse transcriptase (RT), the pol gene protein. Twenty-seven clones were found to produce a high level of the reverse transcriptase produced by 3T3 cells containing the parent plasmid 3PO (FIG. 4). In a separate electroporation, 3PO DNA, containing an intact set of gag, pol, and env genes, was coelectroporated with pSV2gpt into 3T3 cells. Of 16 MA-resistant clones obtained from this electroporation and tested, supernatants from 3 were high in reverse transcriptase (FIG. 4). The reverse transcriptase levels of the high reverse transcriptase-producing GP+E clones were equal to those of the high reverse transcriptase-producing 3PO clones.

Figure 5:
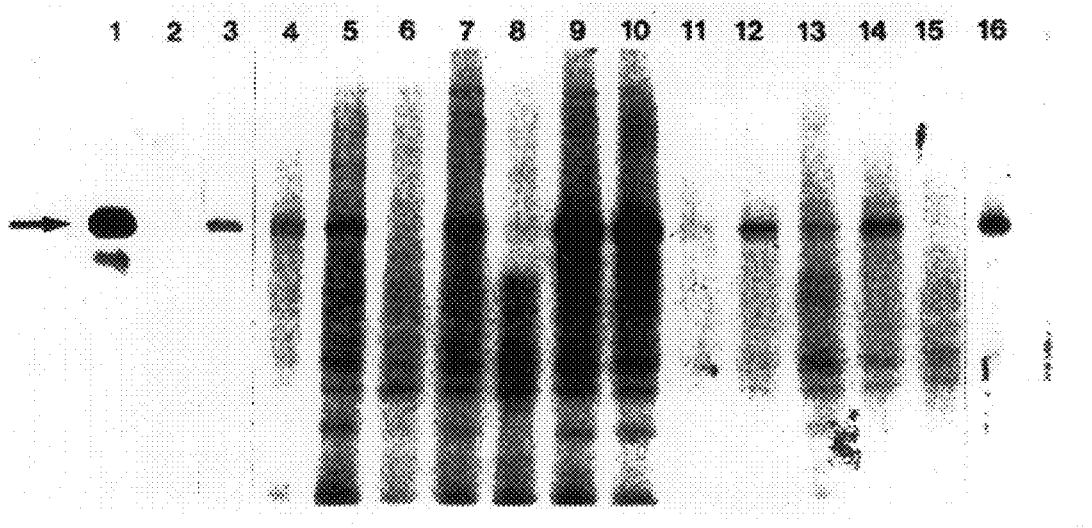
FIG. 5. Analysis of viral env protein synthesis in transfected NIH 3T3 cells. Plasmids pgag-polgpt and penv were cotransfected into 3T3 cells. Individual clones resistant to MA and which express high levels of RT were labelled with [$^{35}$S] methionine. The labelled proteins were analyzed by immunoprecipitation, sodium dodecyl sulfate gel electrophoresis, and fluorography as described in Methods. Lane 1: Proteins from 3PO-18 cells. Lanes 2–16: Proteins from GP+E clones 5, 21, 30, 37, 38, 41, 42, 43, 46, 56, 58, 66, 69, 75 and 86, respectively. The position of protein gPr80$^{env}$ is indicated by the arrow.

Twenty-one of the high RT-producing GP+E clones were then analyzed for env protein expression by metabolic labelling followed by immunoprecipitation with env antiserum (15). Eleven of the clones were positive for gPr80env; 3 clones produced a strong signal, 4 a medium signal, and 4 a weak signal (FIG. 5).

Ability of Cell Lines to Package Retroviral Vectors

Five of the GP+E cell lines which expressed high reverse transcriptase activity and medium-to-high env protein were tested for their ability to package the replication-defective retroviral vector Δneo. Δneo is a 6.6 kb replication-defective retroviral plasmid containing a neomycin resistance gene driven by an SV40 promoter (FIG. 3). Cell lines were transfected with Δneo and G418-resistant clones were collected. Supernatants from G418-resistant were then tested for Δneo viral particles. The titers of GP+EΔneo clones ranged from 2×10$^2$ to 1.7×10$^5$ CFU/ml (Table 1). These titers were comparable to Δneo titers released from the 3PO-18 packaging line, which was constructed by transfecting 3PO into NIH 3T3 cells (8×10$^2$ to 6.5×10$^4$ CFU/ml) as well as from the ψ$^2$ packaging line (6) (4.6×10$^4$–5.4×10$^4$ CFU/ml). The GP+E-86 packaging line produced titers that were consistently higher than the other four GP+E lines, and was, therefore, used in subsequent experiments.

To test the effect of changing the structure of the retroviral vector containing the exogenous gene, in this case, the neomycin-resistance gene, GP+E-86 cells were transfected with the N2 retroviral vector (16) in which neomycin-resistance expression is controlled by the viral LTR (FIG. 3). N2 DNA was electroporated into GP+E-86 cells (CRL 9642), and 22 G418-resistant clones (GP+E+N2) were isolated. G418-resistant clones were tested for N2 virus titer, and titers of 5.0×10$^3$ to 4×10$^6$ CFU/ml were obtained (Table 1). These titers were comparable to N2 titers released from the 3PO-18 cell line (1.85×10$^4$ to 5.0×10$^5$ CFU/ml). Thus, N2 produced titers that were 1–2 logs higher than Δneo, and the packaging line that was constructed was as efficient as one in which all three retroviral components are on the same plasmid.

TABLE 1

VIRUS PRODUCTION FROM PACKAGING CELLS CONTAINING RETROVIRAL VECTORS

| Packaging Cell Line | Vector | # Clones Tested | Titer (CFU/ml) | | |
|---|---|---|---|---|---|
| | | | Range | Median | Mean |
| GP+E-86 | Δneo | 9 | 2 × 10$^2$–1.7 × 10$^5$ | 3.3 × 10$^4$ | 5.4 × 10$^4$ |
| ψ$^2$ | Δneo | 2 | 4.6 × 10$^4$–5.4 × 10$^4$ | NA | NA |
| 3PO-18 | Δneo | 8 | 8 × 10$^2$–6.5 × 10$^4$ | 6.2 × 10$^3$ | 1.47 × 10$^4$ |
| GP+E-18 | N2 | 22 | 5 × 10$^3$–4 × 10$^6$ | 7.5 × 10$^5$ | 1.38 × 10$^6$ |
| 3P0-18 | N2 | 9 | 1.85 × 10$^4$–5 × 10$^5$ | 1 × 10$^5$ | 2.14 × 10$^5$ |
| GP+envAm-12 | N2 | 22 | 3 × 10$^3$–1 × 10$^6$ | 6.75 × 10$^4$ | 1.45 × 10$^5$ |
| PA317 | N2 | 6 | 2 × 10$^3$–2 × 10$^5$ | 1.15 × 10$^5$ | 1.01 × 10$^5$ |

Analysis for Recombinant Infectious Retrovirus

As a preliminary test for infectious retrovirus, supernatants from 5 high-titer GP+E+Δneo clones were used to infect 3T3 cells. The infected 3T3 cells were selected with G418 and allowed to develop into a confluent layer of G418-resistant clones. Supernatants from these plates (2° GP+E+Δneo supernatants) were then used to infect fresh 3T3 cells. These 3T3 cells were again selected with G418 that resulted in no surviving G418-resistant cells. These same supernatants also tested negative for reverse transcriptase. These results indicate that there was no viral rescue of Δneo from the initial 3T3 cells infected with GP+E+Δneo primary supernatants.

As a stringent test for infectious retrovirus which may have been generated through recombination events between the two helper plasmids and the Δneo retroviral vector, 3T3 cells were infected with supernatant from pooled clones containing GP+E-86+Δneo. The infected cells were passaged continuously for one month without G418 selection. This treatment would have allowed a rare wild-type virus to spread throughout the population of 3T3 cells (this population of cells should contain cells successfully infected with Δneo virus as well as uninfected 3T3 cells that are not G418-resistant), and, therefore, led to the spread of infectious Δneo particles. After one month in culture, supernatant was assayed for Δneo virus production by infecting fresh 3T3 cells and testing for G418 resistance. The infected 3T3 cells yielded no G418-resistant clones, indicating that there was no viral rescue of Δneo from the initial 3T3 cells that were infected with GP+E-86+Δneo supernatant.

In a different test of the safety of the GP+E-86 packaging line, supernatant from cells containing GP+E-86 was used to infect pools of N2-transfected 3T3 cells (3T3-N2 pools). If the 3T3-N2 cells became infected with wild-type virus secreted from GP+E-86 cells (CRL 9642), the 3T3-N2 cells would begin to secrete N2 virus. Supernatant from the GP+E-86-infected 3T3-N2 pools was harvested and used to infect fresh 3T3 cells. These 3T3 cells were then tested for the presence of N2 virus by G418 selection. Using the assay G418-resistant cells were not detected, demonstrating that GP+E-86 cells are unable to transfer the packaging function or to rescue N2 virus from 3T3 cells.

Construction of an Amphotropic Packaging Line

Figure 1:
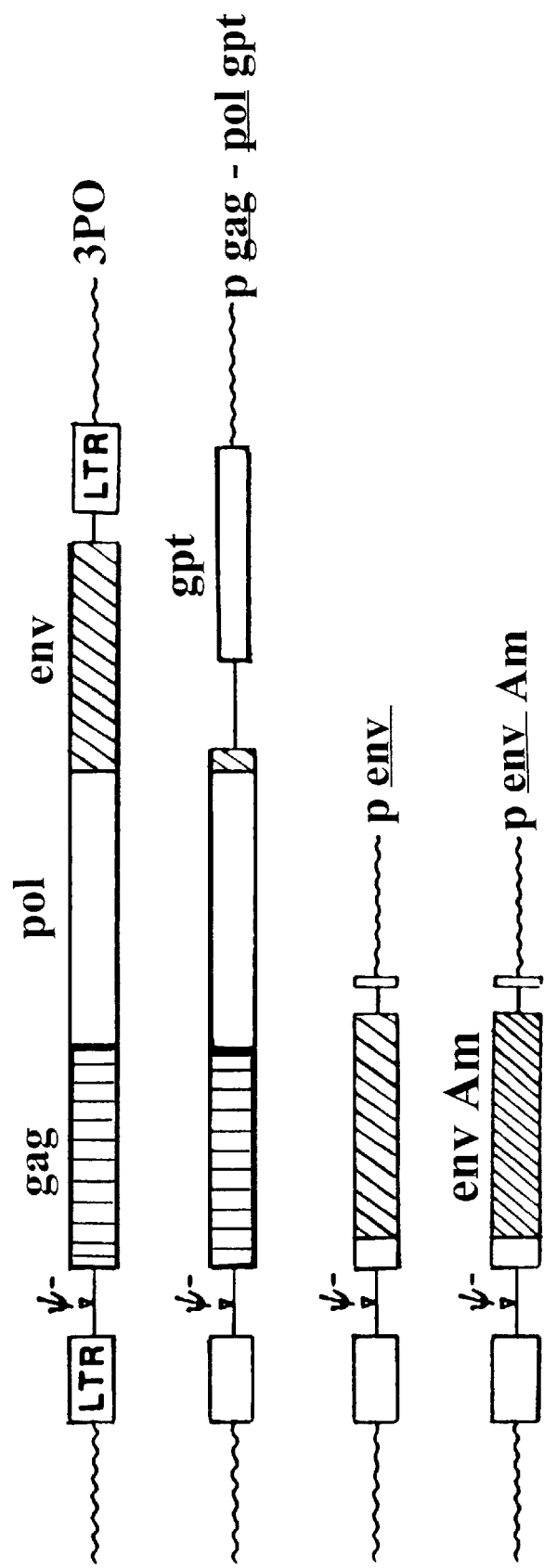
FIG. 1. Comparison of viral sequences contained in parent plasmid 3PO and constructs pgag-polgpt, penv and penvAm. Mo-MULV LTRs and ψ deletion are indicated. Solid regions represent gag sequences; open regions represent pol sequences; hatched regions represent env or envAm sequences; wavy lines represent pBR322 sequences.

To generate a safe amphotropic packaging line the plasmid penvAm was constructed using DNA from pL1 (5), a plasmid containing the 4070A amphotropic murine Leukemia virus proviral DNA. A fragment containing the env gene and 3' acceptor splice site was isolated and ligated to a fragment from 3PO containing the Mo-MULV 5' LTR and 5' donor splice site (FIG. 1). The plasmids penvAm and pRSVhyg (17) were co-transfected into a clone of 3T3 cells that had been transfected with the pgag-polgpt and shown to produce a high level of reverse transcriptase. Hygromycin B-resistant clones were isolated and tested for amphotropic env protein production by metabolic labelling followed by immunoprecipitation with env antiserum. The cell line GP+envAm-12 was selected as a clone producing high levels of both reverse transcriptase and amphotropic env protein. To test packaging ability, GP+envAm-12 cells were transfected with N2. G418-resistant clones were isolated and the titers of released N2 virus were determined by infecting 3T3 cells with harvested supernatants. Titers of GP+envAm-12+N2 clones ranged from $3\times10^3$ to $>1\times10^6$ CFU/ml (Table 1). In a control experiment, N2 was transfected into the amphotropic packaging line PA317 (11). Titers of G418-resistant clones, when used to infect 3T3 cells, range from $2\times10^3$ to $2.0\times10^5$ CFU/ml. The results indicate that GP+envAm-12 is as efficient in retroviral gene transfer as PA317.

Use of Packaging Lines to Generate Producer Lines

Packaging cell lines can be used to construct cell lines that produce helper-free viruses which contain any gene of interest (producer lines) by transfecting retroviral vectors into them. The GP+E-86 ecotropic packaging line (CRL 9642) and the GP+envAm-12 amphotropic packaging line (CRL 9642) can be used to generate safe producer lines as follows: The packaging cell lines are transfected with DNA containing a ψ packaging sequence, a selectable marker, and the gene of interest; for example the β globin or ADA gene. The ψ packaging sequence allows the retroviral vector to be encapsidated into a virus shell using proteins synthesized in the packaging cell line. The selectable marker, such as the neomycin resistance gene, allows for selection of cells successfully transfected or infected with the vector. Individual clones, or pools of clones, containing the transfected vector are selected. These clones secrete the packaged vector virus, and not the defective helper virus, and are known as producer lines. Titering assays are then done to determine the viral titers released by the producer lines.

EXPERIMENTAL DISCUSSION

One of the requirements for the use of retroviral vectors in human gene therapy is the use of a packaging line which is incapable of producing wild-type virus. While recently-designed packaging lines are relatively safe, wild-type virus may be produced through two recombinational events between the helper virus and a replication-defective retroviral vector even with the most frequently used amphotropic line PA317. In order to create a safer packaging line, the gag and pol genes have been separated on one plasmid, and the ecotropic or amphotropic env gene on another plasmid. These plasmids contain deletions of the packaging (ψ) signal and the 3' LTR. An ecotropic packaging line (GP+E-86CRL 9642) and an amphotropic packaging line (GP+envAm-12CRL 9641) have been developed that produce titers of retroviral particles comparable to those packaging lines containing the helper virus genome on a single plasmid.

Both the ecotropic (GP+E-86) and the amphotropic (GP+envAm-12) packaging lines produce high gag-pol and env protein levels, as demonstrated by the reverse transcriptase assay and immunoprecipitation with α env. GP+E-86 cells (which contain gag and pol on one plasmid and env on another plasmid) upon transfection with the retroviral vectors Δneo and N2 release titers that are comparable to the titers released by 3PO-18 and ψ2 cells (which contain an intact gag-pol-env plasmid). These titers obtained are comparable to those reported by others using defective retrovirus (5, 20, 6, 11, 7, 8, 9) and are high enough for use in gene transfer experiments in animals (21, 22, 23, 24, 10, 25, 11, 26, 27).

No evidence has yet been found for the generation of wild-type retrovirus using the GP+E-86 packaging line, either alone or in combination with the replication-defective retroviral vectors Δneo and N2. Thus, no evidence has been found for recombinational events occurring when gag-pol on one plasmid and env on another are used in plasmids that also contain ψ mutations and deletions of 3' LTRs. Cells electroporated with these packaging plasmids and then with vector plasmids do not appear to produce the three recombinational events needed for the generation of wild type virus. Preliminary experiments also demonstrate that the GP+envAm-12 packaging line (CRL 9641) appears to be equally safe and, therefore, appropriate for use in experiments designed for human gene therapy.

REFERENCES

1. Cone, R. D., A. Weber-Benarous, D. Baorto, and R. C. Mulligan. 1987. Regulated expression of a complete 1. human B-globin gene encoded by a transmissible retrovirus vector. *Mol. Cell. Biol.* 7:887–897.
2. Anderson, W. F. 1984. Prospects for human gene therapy. *Science* 226:401–409.
3. Neel, B. B., W. S. Hayward, H. L. Robinson, J. Fang, and S. M. Astrin. 1981. Avian leukosis virus-induced tumors have common proviral integration sites and synthesize discrete new RNAs: Oncogenesis by promoter insertion. *Cell* 23:323–334.
4. Varmus, H. E., N. Quintrell, and S. Ortiz. 1981. Retroviruses as mutagens: Insertion and excision of a nontransforming provirus alter expression of a resident transforming provirus. *Cell* 25:23–36.
5. Cone, R. D., and R. C. Mulligan. 1984. High efficiency gene transfer into mammalian cells: Generation of helper-free retrovirus with broad mammalian host range. *Proc. Natl. Acad. Sci.* 81:6349–6353.
6. Mann, R., F. C. Mulligan, and D. Baltimore. 1983. Construction of a retrovirus packaging mutant and its use to produce helper-free defective retrovirus. *Cell* 33:153–159.
7. Miller, A. D, M. -F. Law, and I. M. Verma. 1985. Generation of helper-free Amphotropic retroviruses that transduce a dominant-acting methotrexate-resistant dihydrofolate reductase gene. *Mol. Cell Biol.* 5:431–437.
8. Sorge, J., D. Wright, V. D. Erdman, and A. Cutting. 1984. Amphotropic retrovirus system for human cell gene transfer. *Mol. Cell. Biol.* 4:1730–1737.
9. Watanabe, S., and H. M. Temin. 1983. Construction of a helper cell line for Avian reticuloendotheliosis virus cloning vectors. *Mol. Cell. Biol.* 3:2241–2249.
10. Hock, R. A., and A. D. Miller. 1986. Retrovirus-mediated transfer and expression of drug-resistant genes in man haematopoietic progenitor cells. *Nature* 320:257–277.
11. Miller, A. D., and C. Buttimore. 1986. Redesign of retrovirus packaging cell lines to avoid recombination leading to helper virus production. *Mol. Cell. Biol.* 6:2895–2902.
12. Mulligan, R. C., and P. Berg. 1980. Expression of a bacterial gene in mammalian cells. *Science* 209:175–183.
13. Potter, H., L. W. Weir, and P. Leder. 1984. Enhancer-dependent expression of human K immunoglobulin genes introduced into mouse pre-B lymphocytes by electroporation. *Proc. Natl. Acad. Sci.* 81:7161–7165.
14. Goff, S. P., P. Traktman, and D. Baltimore. 1981. Isolation and properties of Moloney murine leukemia virus mutants: Use of a rapid assay for release of virion reverse transcriptase. *J. Virol.* 38:239–248.
15. Schwartzberg, P., J. Colicelli, and S. Goff. 1983. Deletion mutants of Moloney murine leukemia virus which lack glycosylated gag protein are replication competent. *J. Virol.* 46:538–546.
16. Keller, G., C. Paige, E. Gilboa, and E. F. Wagner. 1985. Expression of a foreign gene in myeloid and lymphoid cells derived from multipotent haematopoietic precursors. *Nature* 318:149–154.
17. Murphy, A. J. 1987. Molecular techniques for the isolation of transcriptional transacting genes. Doctoral Thesis, Columbia University 133–139.
18. Grunstein, M., and D. S. Hogness. 1975. Colony hybridization: A method for isolation of cloned DNAs that contain a specific gene. *Proc. Natl. Acad. Sci.* 72:3961–3965.
19. Laemmli, U. K. 1970. Cleavage of structural proteins during the assembly of the head of bacteriophage T4. *Nature* 227:680–685.
20. Cone, R. D., A. Weber-Benarous, D. Baorto and R. C. Mulligan. 1987. Regulated expression of a complete human β globin gene encoded by a transmissible retrovirus vector. *Mol. Cell. Biol.* 7:887–897.
21. Cline, M. J., H. Stang, K. Mercola, L. Morse, R. Ruprecht, J. Browne, and W. Salser. 1980. Gene transfer in intact animals. *Nature* 284:422–425.
22. Dick, J. E., M. C. Magli, D. Huszar, R. A. Phillips and A. Bernstein. 1985. Introduction of a selectable gene into primitive stem cells of long-term reconstitution of the hemopoietic system of W/W$^V$ mice. *Cell* 42:71–79.
23. Eglitis, M. A., P. Kantoff, E. Gilboa, and W. F. Anderson. 1985. Gene expression in mice after high efficiency retroviral-mediated gene transfer. *Science* 230:1395–1398.
24. Gruber, H. E., K. D. Finley, R. M. Herschberg, S. S. Katzman, P. K. Laikind, J. E. Seegmiller, T. Friedman, J. Yee and D. J. Jolly. 1985. Retroviral vector-mediated gene transfer into human hematopoietic progenitor cells. *Science* 230:1057–1060.
25. Lemischka, I. R., D. H. Raulet, and R. C. Mulligan. 1986. Developmental potential and dynamic behavior of hematopoietic stem cells. *Cell* 45:917–927.
26. Williams, D. A., I. R. Lemischka, D. G. Nathan and R. C. Mulligan. 1984. Introduction of new genetic material into pluripotent haematopoietic stem cells of the mouse. *Nature* 310:476–480.
27. Williams, D. A., S. H. Orkin and R. C. Mulligan. 1986. Retrovirus-mediated transfer of human adenosine deaminase gene sequences into cells in culture and into murine hematopoietic cells in vivo. *Proc. Natl. Acad. Sci.* 83:2566–2570.

What is claimed is:

1. A mammalian packaging cell which does not produce wildtype recombinant infectious retrovirus and is generated by:
   A) cotransfecting mammalian cells with:
      1) a plasmid comprising a 5' LTR, a gag gene and a pol gene from a virus, and a gene encoding a selectable marker, but not comprising a ψ packaging signal, a 3' LTR, or an env gene from such virus; and
      2) a plasmid comprising a 5' LTR and an env gene from a virus but not comprising a ψ packaging signal, a 3' LTR, a gag gene, or a pol gene from the virus;
   B) identifying a cell from among the transfected cells which expresses the gag and pol genes and binds to an anti-env antibody, so as to identify a cell which expresses the gag, pol and env genes, and obtaining a cell line of such cell,
   C) transfecting cells obtained from the cell line with a retroviral vector and measuring the titer of viral particles produced by such cells so as to thereby identify the cell line as one having cells which package a retroviral vector,
   D) identifying cells from the retroviral packaging cell line which do not produce wildtype recombinant infectious retrovirus, and isolating such cells so as to thereby generate a mammalian packaging cell which does not produce wildtype recombinant infectious retrovirus.

2. A mammalian packaging cell which does not produce wildtype recombinant infectious retrovirus and is generated by:
   A) transfecting mammalian cells with a first plasmid comprising a 5' LTR, a gag gene and a pol gene from a virus, and a gene encoding a selectable marker, but not comprising a ψ packaging signal, a 3' LTR, or an env gene from such virus;

B) identifying a cell from among the cells transfected with the first plasmid which expresses the gag and pol genes, and generating a cell line of such cell;

C) tranfecting cells from the cell line with a second plasmid comprising a 5' LTR and an env gene from a virus but not comprising a ψ packaging signal, a 3' LTR, a gag gene, or a pol gene from the virus;

D) identifying a cell from among the cells transfected with the second plasmid which binds to an anti-env antibody, so as to identify a cell which expresses the gag, pol and env genes, and obtaining a cell line of such cell, E) transfecting cells obtained from the cell line which expresses the gag, pol and env genes with a retroviral vector and measuring the titer of viral particles produced by such cells so as to thereby identify the cell line as one having cells which package a retroviral vector, F) identifying cells from the retroviral packaging cell line which do not produce wildtype recombinant infectious retrovirus, and isolating such cells so as to thereby generate a mammalian packaging cell which does not produce wildtype recombinant infectious retrovirus.

3. A mammalian packaging cell which does not produce wildtype recombinant infectious retrovirus and is generated by:

A) transfecting mammalian cells with a first plasmid comprising a 5' LTR and an env gene from a virus but not comprising a ψ packaging signal, a 3' LTR, a gag gene, or a pol gene from the virus;

B) identifying a cell from among the cells transfected with the first plasmid which binds to an anti-env antibody, so as to identify a cell which expresses the env gene, and obtaining a cell line of such cell, C) tranfecting cells from the cell line with a second plasmid comprising a 5' LTR, a gag gene and a pol gene from a virus, and a gene encoding a selectable marker, but not comprising a ψ packaging signal, a 3' LTR, or an env gene from such virus;

D) identifying a cell from among the cells transfected with the second plasmid which expresses the gag and pol genes env genes, and generating a cell line of such cell;

E) transfecting cells obtained from the cell line which expresses the gag, pol and env genes with a retroviral vector and measuring the titer of viral particles produced by such cells so as to thereby identify the cell line as one having cells which package a retroviral vector, F) identifying cells from the retroviral packaging cell line which do not produce wildtype recombinant infectious retrovirus, and isolating such cells so as to thereby generate a mammalian packaging cell which does not produce wildtype recombinant infectious retrovirus.

4. A method of generating a mammalian packaging cell which does not produce wildtype recombinant infectious retrovirus and is generated by:

A) cotransfecting mammalian cells with:

1) a plasmid comprising a 5' LTR, a gag gene and a pol gene from a virus, and a gene encoding a selectable marker, but not comprising a ψ packaging signal, a 3' LTR, or an env gene from such virus; and 2) a plasmid comprising a 5' LTR and an env gene from a virus but not comprising a ψ packaging signal, a 3' LTR, a gag gene, or a pol gene from the virus;

B) identifying a cell from among the transfected cells which expresses the gag and pol genes and binds to an anti-env antibody, so as to identify a cell which expresses the gag, pol and env genes, and obtaining a cell line of such cell, C) transfecting cells obtained from the cell line with a retroviral vector and measuring the titer of viral particles produced by such cells so as to thereby identify the cell line as one having cells which package a retroviral vector, D) identifying cells from the retroviral packaging cell line which do not produce wildtype recombinant infectious retrovirus, and isolating such cells so as to thereby generate a mammalian packaging cell which does not produce wildtype recombinant infectious retrovirus.

5. A method of generating a mammalian packaging cell which does not produce wildtype recombinant infectious retrovirus and is generated by:

A) transfecting mammalian cells with a first plasmid comprising a 5' LTR, a gag gene and a pol gene from a virus, and a gene encoding a selectable marker, but not comprising a ψ packaging signal, a 3' LTR, or an env gene from such virus;

B) identifying a cell from among the cells transfected with the first plasmid which expresses the gag and pol genes, and generating a cell line of such cell;

C) tranfecting cells from the cell line with a second plasmid comprising a 5' LTR and an env gene from a virus but not comprising a ψ packaging signal, a 3' LTR, a gag gene, or a pol gene from the virus;

D) identifying a cell from among the cells transfected with the second plasmid which binds to an anti-env antibody, so as to identify a cell which expresses the gag, pol and env genes, and obtaining a cell line of such cell, E) transfecting cells obtained from the cell line which expresses the gag, pol and env genes with a retroviral vector and measuring the titer of viral particles produced by such cells so as to thereby identify the cell line as one having cells which package a retroviral vector, F) identifying cells from the retroviral packaging cell line which do not produce wildtype recombinant infectious retrovirus, and isolating such cells so as to thereby generate a mammalian packaging cell which does not produce wildtype recombinant infectious retrovirus.

6. A method of generating a mammalian packaging cell which does not produce wildtype recombinant infectious retrovirus and is generated by:

A) transfecting mammalian cells with a first plasmid comprising a 5' LTR and an env gene from a virus but not comprising a ψ packaging signal, a 3' LTR, a gag gene, or a pol gene from the virus;

B) identifying a cell from among the cells transfected with the first plasmid which binds to an anti-env antibody, so as to identify a cell which expresses the env gene, and obtaining a cell line of such cell, C) tranfecting cells from the cell line with a second plasmid comprising a 5' LTR, a gag gene and a pol gene from a virus, and a gene encoding a selectable marker, but not comprising a ψ packaging signal, a 3' LTR, or an env gene from such virus;

D) identifying a cell from among the cells transfected with the second plasmid which expresses the gag and pol genes env genes, and generating a cell line of such cell;

E) transfecting cells obtained from the cell line which expresses the gag, pol and env genes with a retroviral vector and measuring the titer of viral particles produced by such cells so as to thereby identify the cell line as one having cells which package a retroviral vector, F) identifying cells from the retroviral packaging cell line which do not produce wildtype recombinant infectious retrovirus, and isolating such cells so as to thereby generate a mammalian packaging cell which does not produce wildtype recombinant infectious retrovirus.

* * * * *